United States Patent [19]

Kukolja

[11] 4,093,800

[45] June 6, 1978

[54] PROCESS FOR PREPARING CEPHAM COMPOUNDS

[75] Inventor: Stjepan Kukolja, Indianapolis, Ind.

[73] Assignee: Eli Lilly and Company, Indianapolis, Ind.

[21] Appl. No.: 768,138

[22] Filed: Feb. 14, 1977

Related U.S. Application Data

[62] Division of Ser. No. 615,154, Sep. 19, 1975, Pat. No. 4,024,152.

[51] Int. Cl.$^2$ .............................................. C07D 501/02
[52] U.S. Cl. ....................................... 544/16; 424/246
[58] Field of Search ...................... 260/243 C; 544/16

[56] References Cited

U.S. PATENT DOCUMENTS

| | | | |
|---|---|---|---|
| 3,792,995 | 2/1974 | Ochiai et al. | 544/16 |
| 3,929,775 | 12/1975 | Ochiai et al. | 544/16 |
| 4,008,230 | 2/1977 | Koppel | 544/16 |
| 4,013,650 | 3/1977 | Fechtig | 260/243 C |
| 4,024,152 | 5/1977 | Kukolja | 260/243 C |
| 4,036,835 | 7/1977 | Foglio et al. | 260/243 C |
| 4,052,387 | 10/1977 | Kukolja | 544/16 |
| 4,052,408 | 10/1977 | Heusler et al. | 544/16 |
| 4,058,521 | 11/1977 | Uyeo et al. | 544/16 |

*Primary Examiner*—Nicholas S. Rizzo
*Attorney, Agent, or Firm*—William C. Martens, Jr.; Everet F. Smith

[57] ABSTRACT

A novel 4-(2'-benzothiazolyldithio)-3-imidoazetidin-2-one of the formula

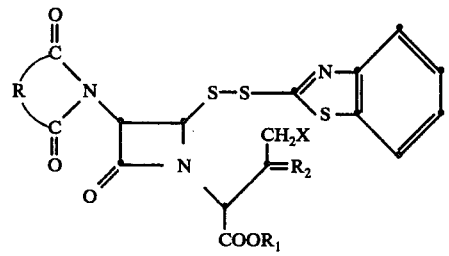

in which X is chloro or bromo and $R_2$ is methylene or oxygen is ring-closed to the corresponding 3-exomethylenecepham or 3-"oxo" cepham by treatment with sodium or potassium iodide at a temperature of from about 40° C. to about 80° C.

11 Claims, No Drawings

PROCESS FOR PREPARING CEPHAM COMPOUNDS

This is a division of application Ser. No. 615,154, filed Sept. 19, 1975, and now U.S. Pat. No. 4,024,152 issued May 17, 1977.

BACKGROUND OF THE INVENTION

The preparation of 3-exomethylenecephams has recently been reported [Chauvette, R. R., and Pennington, P. A., *Journal of Organic Chemistry*, 38, 2994 (1973); and Chauvette, R. R., and Pennington, P. A., *Journal of the American Chemical Society*, 96, 4986 (1974)]. In conjunction with this disclosure, it was also reported that the 3-exomethylenecephems could be converted by ozonolysis to their corresponding 3-"oxo" cephems. These latter compounds can also be termed 3-keto cephems or, in terms of their tautomeric form, 3-hydroxy cephems.

It has now been discovered that 3-exomethylenecephems and 3-ketocephams can be prepared from a novel class of azetidin-2-ones. It is to such a class of compounds as well as to a process for preparing 3-exomethylenecephams and 3-ketocephams from these compounds that this invention is directed.

SUMMARY OF THE INVENTION

It is an object of this invention therefore to provide a process for preparing a 3-exomethylenecepham or a 3-ketocepham (3-hydroxy-3-cephem) which comprises reacting a compound of the formula

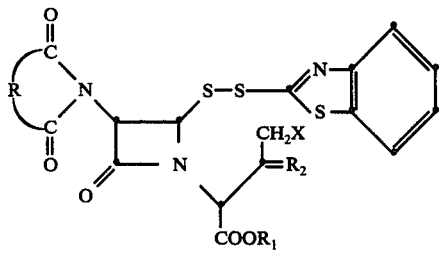

with at least a molar ratio of sodium or potassium iodide at a temperature of from about 40° C. to about 80° C., to produce the aforementioned 3-exomethylene or 3-keto compound of the formula

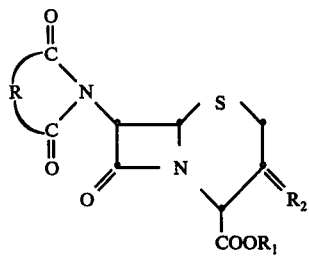

in which, in the above formulae, $R_1$ is a carboxy protecting group; R is the residue of an imide derived from a dicarboxylic acid; $R_2$ is $=CH_2$ or $=O$; and X is chloro or bromo.

Another object of this invention relates to novel azetidin-2-ones of the formula

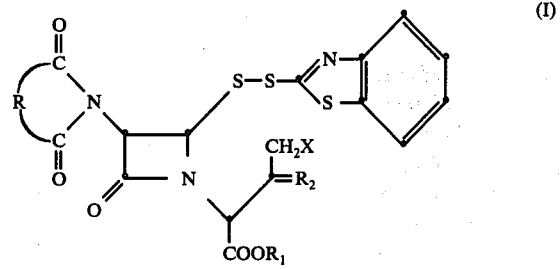

in which R, $R_1$, $R_2$, and X are as defined hereinabove.

DETAILED DESCRIPTION OF THE INVENTION

As delineated hereinabove, the novel azetidin-2-ones of this invention have the formula I above.

$R_1$ in the above formula I denotes a carboxy protecting group. Preferably, the carboxy protecting group is the residue of an ester function which is removable by acid treatment or by hydrogenation. Preferred such carboxy protecting groups include, for example, $C_1$-$C_4$ alkyl, 2-iodoethyl, benzyl, p-nitrobenzyl, succinimidomethyl, phthalimidomethyl, p-methoxybenzyl, benzhydryl, $C_2$-$C_6$ alkanoyloxymethyl, trimethylsilyl, and phenacyl.

Specific illustrations of the preferred carboxy protecting groups of the azetidin-2-ones of this invention include, for example, methyl, ethyl, n-propyl, isopropyl, n-butyl, sec-butyl, isobutyl, t-butyl, 2-iodoethyl, benzyl, p-nitrobenzyl, succinimidomethyl, phthalimidomethyl, p-methoxybenzyl, benzhydryl, acetoxymethyl, pivaloyloxymethyl, propionoxymethyl, trimethylsilyl, phenacyl, and the like.

Highly preferred carboxy protecting groups are methyl, benzyl, p-nitrobenzyl, p-methoxybenzyl, benzhydryl, t-butyl, and trimethylsilyl.

The cyclic imide radical, defined by R taken together with the nitrogen-dicarbonyl combination to which it is bonded, can be formed by reacting the amino group of the 6-amino-penam or the 7-amino-cepham precursor further elaborated hereinafter with a dicarboxylic acid or anhydride or other reactive variant thereof, followed by reacting the resulting derivative with a $C_1$-$C_4$ alkyl haloformate, for example, ethyl chloroformate, in the presence of an organic base. Preferably, R is $C_2$-$C_4$ alkylene, 1,2-cyclohexylene, 1,2-phenylene, 1,2-cyclohexenylene, or a substituted derivative of any of these having a substituent selected from the group consisting of $C_1$-$C_3$ alkyl, $C_1$-$C_3$ alkoxy, nitro, fluoro, chloro, bromo, and iodo. Typically, R is the residue of a $C_4$-$C_{10}$ dicarboxylic acid, and the cyclic imide thus represented is prepared from such discarboxylic acid, its anhydride, or an appropriate reactive variant thereof. Cyclic imides can be prepared, for example, from acids such as malonic, succinic, adipic, glutaric, phthalic, and the like, or their respective anhydrides, as well as from cyclohexane-1,2-dicarboxylic, 3-cyclohexene-1,2-dicarboxylic, halogen substituted dicarboxylic acids or anhydrides such as 4-chlorophthalic, 3-iodophthalic, 4-bromophthalic, nitro substituted dicarboxylic acids and anhydrides such as 3-nitrophthalic acid, alkyl substituted dicarboxylic acids and anhydrides such as 4-methylphthalic acid, as well as related compounds and compounds of similar reactivities. Additional examples of cyclic anhydrides of the type defined are found in the prior art such as in the *Journal of Organic Chemistry*, 26, pp. 3365–3367 (September, 1961).

The novel azetidin-2-ones of this invention are useful as intermediates in the production of 3-exomethylenecephams as well as 3-hydroxy-3-cephems. The azetidin-2-ones of this invention are prepared indirectly from 2β-halomethyl-3α-methylpenams which are available in accordance with the methods delineated in Kukolja, S. et al., *Journal of the American Chemical Society*, 97, pp. 3192–3198 (1975). The 2β-halomethyl-2α-methylpenams have the formula

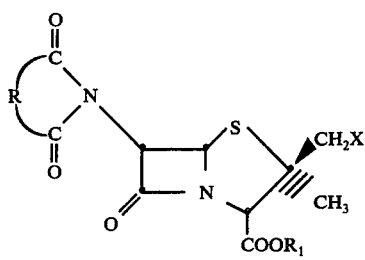

(II)

In accordance with the methods of Kukolja et al., the halomethylpenams are prepared from penicillins by oxidation to their corresponding penicillin sulfoxides. The latter, upon treatment with the thionyl chloride and triethylamine in boiling carbon tetrachloride, produce compound II above in which X is chloro.

Thermolysis of the penicillin sulfoxide to produce the corresponding sulfenic acid, and treatment of the latter with phosphorus tribromide in dichloromethane at room temperature produces a compound of formula II above in which X is bromo.

In addition, Kukolja et al., supra, describe the reaction of a compound of formula

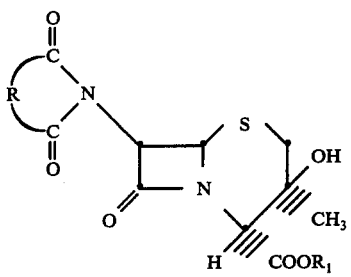

(III)

with thionyl chloride in the presence of triethylamine to produce a compound of formula II above in which X is chloro.

As the Kukolja et al. publication indicates, the compounds of formula II exhibit a lack of stability, rearranging over a period of time to the corresponding 3β-halo-3α-methylcephams. Therefore, the possibility to use these compounds as precursors to the intermediate azetidin-2-ones of this invention is fleeting, and their conversion to the azetidine-2-ones of this invention must be carried out reasonably soon after preparation.

Once the compounds of formula II have been prepared, their conversion to the intermediate azetidin-2-ones of this invention is accomplished by the following sequence:

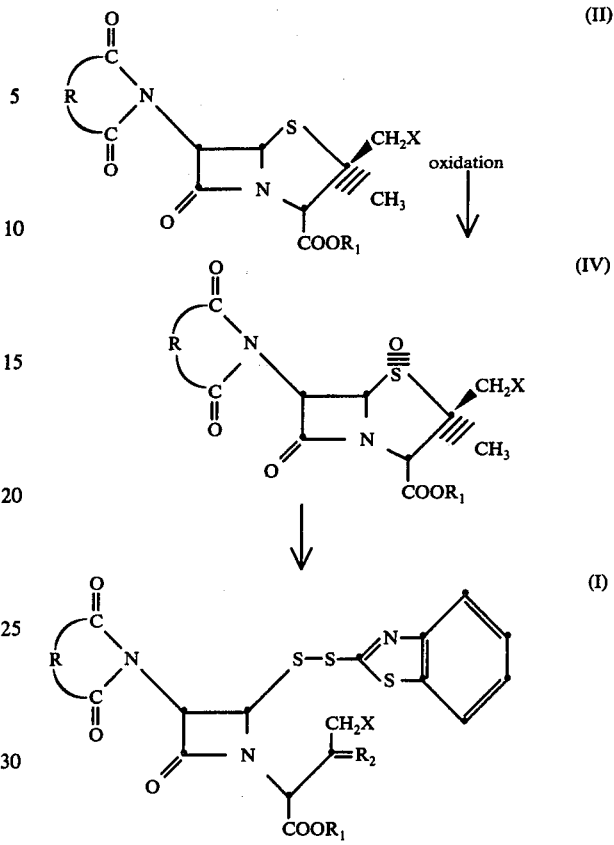

The first step in the sequence involves the oxidation of an ester of a 6-imido-2β-halomethyl-2α-methylpenam-3-carboxylic acid II to the corresponding sulfoxide. This oxidation is carried out in accordance with the well-recognized techniques employed in oxidation of a typical penicillin to its corresponding penicillin sulfoxide. Thus, the halomethylpenam is reacted in an appropriate solvent with a molar equivalent of m-chloroperbenzoic acid, the reaction typically being carried out at a low temperature. The reaction is monitored by means of thin-layer chromatography (TLC) which permits a periodic and current measure of the extent of conversion from the sulfide to the corresponding sulfoxide. When TLC confirms that the reaction is essentially complete, the resulting reaction mixture is worked up in accordance with recognized techniques to recover the desired product.

The product, an ester of a 6-imido-2β-halomethyl-2α-methylpenam-3-carboxylate-1α-oxide (IV), then is converted to the azetidin-2-one of this invention. The azetidin-2-one is prepared by reacting the α-sulfoxide (IV) with 2-mercaptobenzothiazole at an elevated temperature. The reaction is carried out by mixing from about 0.9 to about 1.5 moles and, preferably, about 1.0 to about 1.1 moles, of the mercapto compound with each mole of the halomethylpenam sulfoxide ester. The resulting mixture, preferably dissolved in a suitable inert solvent, is heated to a temperature of from about 40° C. to about 110° C., and preferably from about 70° C. to about 90° C. Suitable solvents are those having a boiling point at least as high as the temperature of reaction. Included among such solvents are, for example, aromatic hydrocarbons such as benzene and toluene; halogenated hydrocarbons such as carbon tetrachloride, chlorobenzene, bromobenzene, bromoform, chloroform, ethylene dichloride, ethylene dibromide, and the like; amides, such as N,N-dimethylformamide, N,N-dimethylacetamide, and the like; aliphatic nitriles, such as acetonitrile, propionitrile, and the like; esters, such as ethyl acetate, and the like; ethers, such as dioxane, and the like; and any other appropriate inert solvents. Preferred solvents are those having a boiling point within the range of the temperature at which the reaction is to be carried out, thereby permitting the reaction mixture to be refluxed while retaining temperature control.

The resulting reaction mixture generally is heated at a temperature in the defined range for a period of from about 0.5 to about 4 hours, and preferably for a period of from about 0.5 to about 1.5 hours. The product which forms generally crystallizes from the reaction mixture and can be readily filtered off. However, the novel azetidin-2-one intermediate also can be isolated from the reaction mixture by evaporating the reaction mixture in vacuo to remove solvent from the system and treating the residue in accordance with readily recognized techniques including extraction, recrystallization, chromatography, and the like.

The azetidin-2-ones which result from the aforedescribed reaction have the formula I above and specifically are those compounds in which the group $R_2$ of the broad definition of the compounds of this invention is methylene. These azetidin-2-ones represent one facet of the invention of this application. For the sake of convenience these azetidin-2-ones will be referred to herein by the shorthand term "methylene azetidinones".

Examples of methylene azetidinones of this invention include: 4-(2'-benzothiazolyldithio)-3-phthalimido-1-(1'-methoxycarbonyl-2'-chloromethylprop-2'-enyl)azetidin-2-one; 4-(2'-benzothiazolyldithio)-3-phthalimido-1-[1'-(p-nitrobenzyloxycarbonyl)-2'-bromomethylprop-2'-enyl]azetidin-2-one; 4-(2'-benzothiazolyldithio)-3-phthalimido-1-[1'-(p-nitrobenzyloxycarbonyl)-2'-chloromethylprop-2'-enyl]azetidin-2-one; 4-(2'-benzothiazolyldithio)-3-succinimido-1-(1'-benzyloxycarbonyl-2'-chloromethylprop-2'-enyl)azetidin-2-one; 4-(2'-benzothiazolyldithio)-3-phthalimido-1-(1'-benzhydryloxycarbonyl-2'-bromomethylprop-2'-enyl)azetidin-2-one; 4-(2'-benzothiazolyldithio)-3-glutarimido-1-[1'-(t-butyloxycarbonyl)-2'-chloromethylprop-2'-enyl]azetidin-2-one; 4-(2'-benzothiazolyldithio)-3-adipimido-1-[1'-(p-nitrobenzyloxycarbonyl)-2'-chloromethylprop-2'-enyl]azetidin-2-one; 4-(2'-benzothiazolyldithio)-3-(3'-bromophthalimido)-1-(1'-benzhydryloxycarbonyl-2'-bromomethylprop-2'enyl)-azetidin-2-one; 4-(2'-benzothiazolyldithio)-3-(4'-iodophthalimido)-1-[1'-(p-nitrobenzyloxycarbonyl)-2'-chloromethylprop-2'-enyl]azetidin-2-one; 4-(2'-benzothiazolyldithio)-3-(3'-methylphthalimido)-1-[1'-(p-methoxybenzyloxycarbonyl)-2'-2'-bromomethylprop-2'enyl]azetidin-2-one; 4-(2'-benzothiazolyldithio)-3-(4'-chlorophthalimido)-1-(1'-phthalimidomethoxycarbonyl-2'-chloromethylprop-2'-enyl)azetidin-2-one; 4-(2'-benzothiazolyldithio)-3-hexahydrophthalimido-1-(1'-succimidomethoxycarbonyl-2'-bromomethylprop-2'-enyl)acetidin-2-one; 4-(2'-benzothiazolyldithio)-3-malonimido-1-[1'-(2'-iodoethoxycarbonyl)-2'-chloromethylprop-2'-enyl]-azetidin-2-one; 4-(2'-benzothiazolyldithio)-3-(1',2',3',6'-tetrahydrophthalimido)-1-(1'-pivaloyloxymethoxycarbonyl-2'-bromomethylprop-2'-enyl)azetidin-2-one; 4-(2'-benzothiazolyldithio)-3-(3'-methylphthalimido)-1-(1'-acetoxymethoxycarbonyl-2'-chloromethylprop-2'-enyl)azetidin-2-one; 4-(2'-benzothiazolyldithio)-3-(4'-methoxyphthalimido)-1-(1'-phenacyloxycarbonyl-2'-bromomethylprop-2'-enyl)azetidin-2-one; 4-(2'-benzothiazolyldithio)-3-methylmalonimido-1-[1'-(p-nitrobenzyloxycarbonyl)-2'-bromomethylprop-2'-enyl]-azetidin-2-one; 4-(2'-benzothiazolyldithio)-3-(4'-fluorophthalimido)-1-[1'-(p-nitrobenzyloxycarbonyl)-2'-chloromethylprop-2'-enyl]-azetidin-2-one; 4-(2'-benzothiazolyldithio)-3-(3'-isopropylphthalimido)-1-[1'-(p-nitrobenzyloxycarbonyl)-2'-chloromethylprop-2'-enyl]azetidin-2-one; 4-(2'-benzothiazolyldithio)-3-(3'-fluorophthalimido)-1-[1'-(p-methoxybenzyloxycarbonyl)-2'-chloromethylprop-2'-enyl]azetidin-2-one; 4-(2'-benzothiazolyldithio)-3-(1',4',5'6'-tetrahydrophthalimido)-1-[1'-(p-nitrobenzyloxycarbonyl)-2'-chloromethylprop-2'-enyl]azetidin-2-one; and the like.

Another facet of this invention comprises those azetidin-2-ones in which the group $R_2$ is oxygen, thereby defining a carbonyl moiety. Compounds in which $R_2$ is oxygen also participate in the invention of this application and have the formula

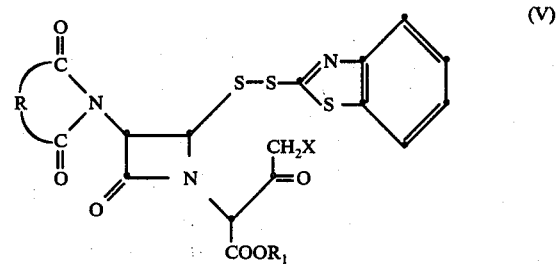

The azetidin-2-ones of formula V are prepared from the methylene azetidinones. Those azetidin-2-ones will be referred to herein by the shorthand term "keto azetidinones". As indicated, the keto azetidinones are prepared from the methylene azetidinones. This conversion is achieved by ozonolysis of the methylene azetidinone followed by decomposition of the ozonide intermediate which is formed.

The aforementioned ozonolysis reaction can be depicted by the following sequence:

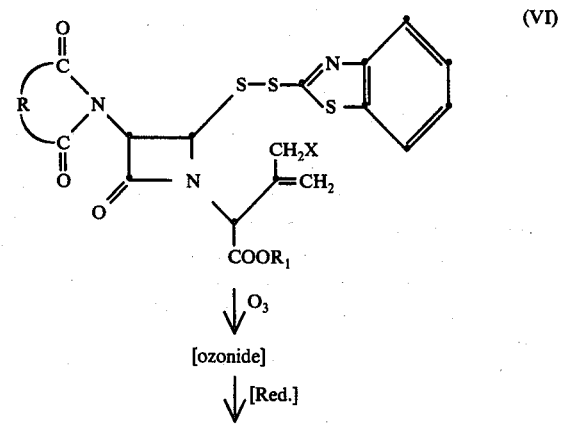

-continued

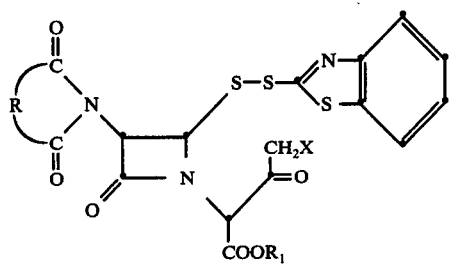
(V)

Specifically, this reaction can be carried out by passing ozone through a solution of the methylene azetidinone (VI) in an inert solvent at a temperature of from about −80° C. to about 0° C. The methylene double bond reacts with ozone to form in situ an intermediate ozonide which is decomposed, as hereinafter described, to form the keto azetidinone of Formula V. In the above formulae, R, R₁, and Z are as hereinbefore described.

Ozone is prepared by means of an ozone generator of the type commonly used in synthetic and analytical chemical work. The ozone is produced by the action of an electric discharge on oxygen. One such ozone generator is that manufactured by the Welsback Corporation. The ozone is generated in a stream of oxygen which then is passed directly into the reaction vessel. The percentage of ozone contained in the oxygen stream can be varied as desired, for example, by varying the rate of flow of oxygen through the ozonizer as well as by varying the intensity of the electric discharge. The percentage of ozone in the oxygen stream can be determined iodimetrically. The amount of iodine liberated by the generated ozone from a standard solution of potassium iodide is determined by titration with sodium thiosulfate. The percentage of ozone in the oxygen stream is not critical; however, for convenience in carrying out the ozonolysis, an estimate of the amount of ozone flowing into the reaction mixture enables one to determine the time at which the desired reaction should be complete and thus minimizes any possibility of formation of over-oxidation products.

Alternatively, the ozonolysis reaction can be followed chromatographically. For instance, a small aliquot of the reaction mixture is withdrawn, the ozonide is decomposed, and the amount of unreacted starting material and keto azetidinone product present in the sample is assessed by a comparison of the thin-layer chromatogram with that of a known amount of starting material and keto azetidinone compound.

Inert solvents which can be used in the ozonolysis reaction are those solvents in which the methylene azetidinone is at least partially soluble and which are unreactive with ozone under the defined conditions. Commonly used organic solvents such as methanol, ethanol, ethyl acetate, methyl acetate, and methylene chloride are satisfactory. The concentration of the methylene azetidinone starting material in the inert solvent is not critical, and it is preferred to use a solvent volume sufficient to form complete solution. Preferably, the temperature of reaction for the ozonolysis is at the lower range, generally between about −80° C. and about −50° C.

When ozonide formation is complete, as determined by any of the methods described above, any excess ozone present in the reaction mixture is purged from the mixture by bubbling nitrogen or oxygen through the mixture.

Following the removal of excess ozone, the ozonide is decomposed by adding to the reaction mixture a mild reducing agent such as sodium bisulfite, sulfur dioxide, trimethyl phosphite, dimethyl sulfide, and the like, to provide the corresponding keto azetidinone product. The decomposition is carried out by adding an excess of the reducing agent to the mixture and then stirring the reaction mixture at a temperature of from about −80° C. to about 0° C. until the reaction mixture is negative to a potassium iodide-starch test.

A preferred reagent for decomposing the intermediate ozonide is gaseous sulfur dioxide. This reagent is preferred since it is completely volatilized from the reaction mixture during the subsequent work-up and thus does not complicate the recovery of the reaction product.

The keto azetidinone product is recovered from the reaction mixture by first evaporating the mixture to dryness and then extracting the product from the residue. Alteratively, the product can be recovered from the organic liquid phase of the decomposition mixture by separating the liquid phase from insolubles, and, after washing and drying, evaporating the organic layer to yield the keto azetidinone product.

In addition, it is pointed out that a tautomer of the keto azetidinone can be drawn, the relationship being depicted as follows:

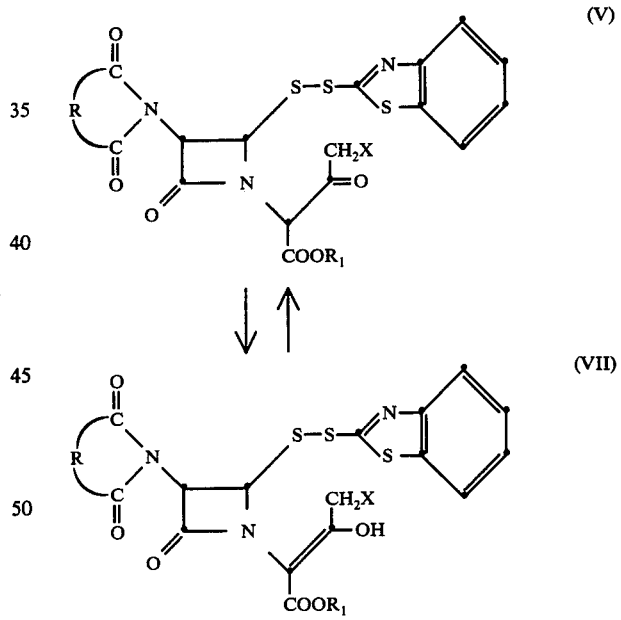

For the purposes of convenience and clarity, however, the above compounds will be referred to herein in their keto form.

Examples of ketoazetidin-2-ones of this invention include: 4-(2'-benzothiazolyldithio)-3-phthalimido-1-(1'-methoxycarbonyl-2'-oxo-3'-chloropropyl)azetidin-2-one; 4-(2'-benzothiazolyldithio)-3-phthalimido-1-[1'-(p-methoxybenzyloxycarbonyl)-2'-oxo-3'-bromopropyl]azetidin-2-one; 4-(2'-benzothiazolyldithio)-3-phthalimido-1-[1'-(p-nitrobenzyloxycarbonyl)-2'-oxo-3'-chloropropyl]azetidin-2-one; 4-(2'-benzothiazolyldithio)-3-succinimido-1-(1'-benzyloxycarbonyl-2'-oxo-3'-chloropropyl)azetidin-2-one; 4-(2'-benzothiazolyldithio)-3-phthalimido-1-(1'-benzhydryloxycarbonyl-2'-oxo-3'-bromopropyl)azetidin-2-one; 4-(2'-benzothiazolyldithio)-3-glutarimido-1-[1'-(t-butyloxycarbonyl)-2'-oxo-3'-chloropropyl]azetidin-2-one; 4-(2'-benzothiazolyldithio)-3-adipimido-1-[1'-(p-nitrobenzyloxycarbonyl)-2'-oxo-3'-chloropropyl]azetidin-2-one; 4-(2'-benzothiazolyldithio)-3-(3'-bromophthalimido)-1-(1'-benzhydryloxycarbonyl-2'-oxo-3'-bromopropyl)azetidin-2-one; 4-(2'-benzothiazolyldithio)-3-(4'-iodophthalimido)-1-[1'-(p-nitrobenzyloxycarbonyl)-2'-oxo-3'-chloropropyl]azetidin-2-one; 4-(2'-benzothiazolyldithio)-3-(3'-methylphthalimido)-1-[1'-(p-methoxybenzyloxycarbonyl)-2'-bromopropyl]azetidin-2-one; 4-(2'-benzothiazolyldithio)-3-(4'-chlorophthalimido)-1-(1'-phthalimidomethoxycarbonyl-2'-oxo-3'-chloropropyl)-azetidin-2-one; 4-(2'-benzothiazolyldithio)-3-hexahydrophthalimido-1-(1'-succinimidomethoxycarbonyl-2'-oxo-3'-bromopropyl)azetidin-2-one; 4-(2'-benzothiazolyldithio)-3-malonimido-1-[1'-(2''-iodoethoxycarbonyl)-2'-oxo-3'-chloropropyl]azetidin-2-one; 4-(2'-benzothiazolyldithio)-3-(1',2',3',6'-tetrahydrophthalimido)-1-(1'-pivaloyloxymethoxycarbonyl-2'-oxo-3'-bromopropyl)azetidin-2-one; 4-(2'-benzothiazolyldithio)-3-(3'-methylphthalimido)-1-(1'-acetoxymethoxycarbonyl-2'-oxo-3'-chloropropyl)azetidin-2-one; 4-(2'-benzothiazolyldithio)-3-(4'-methoxyphthalimido)-1-(1'-phenacyloxycarbonyl-2'-oxo-3'-bromopropyl)azetidin-2-one; 4-(2'-benzothiazolyldithio)-3-methylmalonimido-1-[1'-(p-nitrobenzyloxycarbonyl)-1'-oxo-3'-bromopropyl]-azetidin-2-one; 4-(2'-benzothiazolyldithio)-3-glutarimido-1[1'-(p-nitrobenzyloxycarbonyl)-2'-oxo-3'-chloropropyl]-azetidin-2-one; 4-(2'-benzothiazolyldithio)-3-(3'-isopropylphthalimido)-1-[1'-(p-nitrobenzyloxycarbonyl)-2'-oxo-3'-chloropropyl]azetidin-2-one; 4-(2'-benzothiazolyldithio)-3-(3'-fluorophthalimido)-1-[1'-(p-methoxybenzyloxycarbonyl)-2'-oxo-3'-chloropropyl]-azetidin-2-one; 4-(2'-benzothiazolyldithio)-3-(1',4',5',6'-tetrahydrophthalimido)-1-[1'-p-nitrobenzyloxycarbonyl)-2'-oxo-3'-chloropropyl)-azetidin-2-one; and the like.

The azetidin-2-ones of this invention are useful as intermediates in the preparation of the corresponding 3-exomethylenecephams and 3-ketocephams. This conversion is accomplished in accordance with the following sequence:

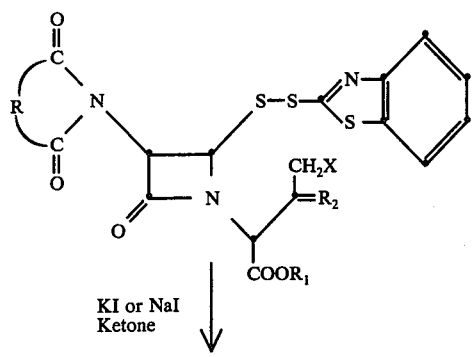

KI or NaI
Ketone

-continued

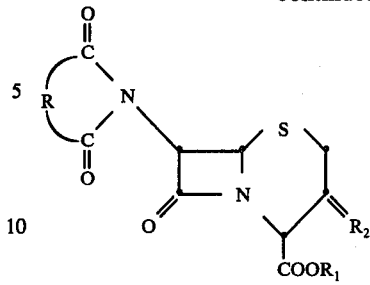

As is true with respect to the ketoazetidin-2-one, the 3-ketocepham ($R_2$ equals oxygen) also gives rise to a tautomerism. Thus, the 3-ketocepham can be drawn in the form of its 3-hydroxy-3cephem structure.

In carrying out the ring-closure of the azetidin-2-one of this invention, the compound generally is reacted with sodium iodide or potassium iodide in a ketone solvent. Typical such ketone solvents include acetone, methyl ethyl ketone, and the like. The solvent preferred for use is acetone. The azetidin-2-one is dissolved in a suitable quantity of the selected solvent. At least a molar quantity of the iodide salt is added and, generally, an excess representing approximately a 2:1 molar ratio of the iodide salt to the azetidin-2-one starting material is employed. The reaction mixture is heated to a temperature from about 40° C. to about 80° C. and preferably to a temperature within the range from about 50° C. to about 60° C., and the resulting mixture is allowed to react at the selected temperature for a period of from about 24 hours to about 48 hours. Generally, the reaction is complete after about 40 hours. The extent of reaction can be monitored quite conveniently by thin-layer chromatograpny (TLC) analysis of an aliquot of the reaction mixture at appropriate points during the course of the reaction.

The product is recovered from the reaction mixture in accordance with well-recognized techniques which may include evaporation of the solvent and extractive separation of the product from the residue which remains.

As indicated above, the structure of the product will be either a 3-exomethylenecepham or a 3-ketocepham depending upon the identity of the group $R_2$ in the azetidin-2-one starting material. In the event that the product which is obtained is a 3-exomethylenecepham, this product can be converted in accordance with known techniques to the corresponding 3-ketocepham compound. These techniques involve ozonolysis of the 3-exomethylenecepham under conditions substantially identical to those delineated hereinabove for conversion of the methylene azetidin-2-one to its corresponding keto azetidin-2-one.

The 3-exomethylenecephams and the 3-ketocephams (3-hydroxy-3-cephems) prepared from the azetidin-2-ones of this invention are well recognized in the art as useful in the production of antibiotically active compounds. These compounds and their utility are described in detail in Chauvette, R. R., and Pennington, P. A., *Journal of Organic Chemistry*, 38, 2994 (1973); and Chauvette, R. R., and Pennington, P. A., *Journal of the American Chemical Society*, 96, 4986 (1974).

The invention of this application is illustrated by the examples which follow. It is not intended that the invention in any way be limited by reason of the following examples.

EXAMPLE 1

Preparation of Methyl 6-phthalimido-2β-chloromethyl-2α-methylpenam-3-carboxylate.

To 500 ml. of dry carbon tetrachloride were added 10 grams of methyl 7-phthalimido-3β-hydroxy-3α-methylcepham-4-carboxylate and 3.43 ml. of thionyl chloride. The resulting mixture was heated to reflux, and 4.26 ml. of triethylamine in 100 ml. of carbon tetrachloride were added over a 1-hour period. The above sequence was repeated using a separate batch of materials, and the resulting reaction mixtures were combined and evaporated to dryness. The residue was taken up in 250 ml. of ethyl acetate, and the ethyl acetate solution was washed twice with 250 ml. of water and then with 25 ml. of brine. The mixture then was dried over magnesium sulfate and evaporated to about one-half volume. A tan powder precipitated and was collected by filtration. The filtrate was then evaporated to dryness, and the residue was recrystallized from a 1:5 mixture of ethyl acetate and ethyl ether to obtain 11.22 grams of the title compound.

EXAMPLE 2

Preparation of Methyl 6-phthalimido-2β-chloromethyl-2α-methylpenam-3-carboxylate-1α-oxide.

To 200 ml. of methylene chloride were added 11.22 grams (28.4 mmoles) of methyl 6-phthalimido-2β-chloromethyl-2α-methylpenam-3-carboxylate. Methylene chloride (100 ml.) containing 5.68 grams (28.4 mmoles) of m-chloroperbenzoic acid was added, and the resulting mixture was stirred for one hour at ice bath temperature. The reaction mixture then was washed successively with 50 ml. of 5 percent aqueous sodium sulfite, twice with 50 ml. of 5 percent sodium bicarbonate, 100 ml. of water, and 100 ml. of brine. The mixture then was dried over magnesium sulfate and evaporated to give 11.54 grams (28.1 mmoles) of the title compound.

NMR (CDCl$_3$) δ 1.41 (s, —CH$_3$), 3.81 (s,—OMe), 4.14 (s,—CH$_2$Cl), 4.92 (s, H-3), 4.96 (d, 1H, J=4.5 Hz.) 5.93 (d, 1H, J=4.5 Hz., and 7.81 Hz. (m, 4 aromatic H).

EXAMPLE 3

Preparation of 4-(2'-Benzothiazolyl-dithio)-3-phthalimido-1-(1'-methoxycarbonyl-2'-chloromethyl-prop-2'-enyl)azetidin-2-one.

To 150 ml. of benzene were added 11.54 grams (28.1 mmoles) of methyl 6-phthalimido-2β-chloromethyl-2α-methylpenam-3-carboxylate-1α-oxide. To the resulting mixture then were added 4.7 grams (28.1 mmoles) of 2-mercaptobenzothiazole. The mixture was heated to reflux for 30 minutes, and the resulting mixture then was evaporated to give the title compound as a light yellow foam.

NMR (CDCl$_3$) δ 3.81 (s,—OMe), 4.3 and 4.5 (dd, —CH$_2$Cl, J=12 Hz.), 5.43 (s, 1H), 5.53 (s, 1H), 5.65 (s, 1H), 5.98 (s, 2 azet. H) and 7.81 Hz (m, 4 aromatic H).

EXAMPLE 4

Preparation of Methyl 7-Phthalimido-3-methylenecepham-4-carboxylate.

To a solution of 1.12 grams (2 mmoles) of 4-(2'-benzothiazolyldithio)-3-phthalimido-1-(1'-methoxycarbonyl-2'-chloromethylprop-2'-enyl)azetidin-2-one in 75 ml. of acetone was added 0.50 grams (3 mmoles) of potassium iodide. The mixture was refluxed for three days after which TLC of the reaction mixture showed a spot indicating the presence of unreacted starting material. An additional 0.5 grams of potassium iodide was added, and refluxing was continued for an additional day during which time TLC established that no change in the reaction mixture was effected. The mixture was evaporated to dryness, and the residue was taken up in 50 ml. of ethyl acetate. The ethyl acetate solution was washed successively with 25 ml. of 0.1 N sodium bisulfite solution, 25 ml. of water, and 25 ml. of brine. The ethyl acetate solution then was dried over sodium sulfate and evaporated to give 1.05 grams of the title compound as a tan foam.

NMR (CDCl$_3$) δ 3.35 and 3.6 (dd, —CH$_2$S, J=13 Hz.), 3.8 (s,—OMe), 5.3 (m, 3H), 5.5 (d, 1H, J=4.5 Hz.), 5.68 (d, 1H, J=4.5 Hz.) and 7.8 Hz. (m, 4 aromatic H).

EXAMPLE 5

Preparation of 4-(2'-Benzothiazolyldithio)-3-phthalimido-1-(1'-methoxycarbonyl-2'-oxo-3'-chloropropyl)azetidin-2-one.

A solution of 1.12 g. (2 mmole) of 4-(2'-benzothiazolyldithio)-3-phthalimido-1-(1'-methoxycarbonyl-2'-chloromethylprop-2'-enyl)azetidin-2-one in 100 ml. of CH$_2$Cl$_2$ was cooled in an acetone-dry ice bath and ozone was introduced into this solution from a generator for 5 minutes. In order to reduce a formed ozonide, sulfur dioxide gas was passed through the solution for 2 minutes. The mixture then was warmed to room temperature and was washed with water and brine. After drying over MgSO$_4$, the solvent was evaporated to give 870 mg. of the title compound.

NMR (CDCl$_3$) δ 3.75 (s,—OMe), 4.45 and 4.75 (dd, —CH$_2$Cl, J=12 Hz.), 5.78 (d, 1H, J=5 Hz.), and 5.97 Hz. (d, 1H, J=5 Hz.).

EXAMPLE 6

Preparation of Methyl 7-Phthalimido-3-ketocepham-4-carboxylate.

A solution of 870 mg. of 4-(2'-benzothiazolyldithio)-3-phthalimido-1-(1'-methoxycarbonyl)-2'-oxo-3'-chloropropyl)azetidin-2-one and 500 mg. of potassium iodide in 40 ml. of acetone was refluxed for 20 hours. The solvent was evaporated, and the residue was dissolved in a mixture of 50 ml. of ethyl acetate and 10 ml. of brine and dried over MgSO$_4$. The solvent was evaporated to give methyl 7-phthalimido-3-keto-cepham-4-carboxylate.

NMR (CDCl$_3$) δ 2.93 and 4.07 (dd,—CH$_2$S, J=15 Hz.), 3.8 (s, 3, —OMe), 5.22 d, 1H, J=4.5 Hz.) 5.75 d, 1H, J=4.5 Hz.), and 7.8 Hz. (m, 4 aromatic H).

EXAMPLE 7

Preparation of p-Nitrobenzyl 6-Phthalimido-2β-bromomethyl-2α-methylpenam-3-carboxylate-1α-oxide.

To about 20 ml. of chloroform were added about one gram of p-nitrobenzyl 6-phthalimido-2β-bromomethyl-2α-methylpenam-3-carboxylate. The resulting solution was cooled in an ice bath, and 500 mg. (2.5 mmoles) of m-chloroperbenzoic acid in 10 ml. of chloroform were added dropwise. The resulting mixture was stirred in the ice bath for about 1 hour. The mixture then was washed successively with 50 ml. of 5 percent sodium bisulfite, twice with 50 ml. of saturated aqueous sodium bicarbonate, with 50 ml. of water, and with 25 ml. of brine. The mixture then was dried over magnesium sulfate and evaporated in vacuo at 25° C. to give the title compound as a white foam.

EXAMPLE 8

Preparation of
4-(2'-Benzothiazolyl-dithio)-3-phthalimido-1-[1'-(p-nitrobenzyloxycarbonyl)-2'-bromomethylprop-2'-enyl]-azetidin-2-one.

A mixture of 1.15 grams (2 mmoles) of p-nitrobenzyl-6-phthalimido-2$\beta$-bromomethyl-2$\alpha$-methylpenam-3-carboxylate-1$\alpha$-oxide and 340 mg. (2 mmoles) of 2-mercaptobenzothiazole in 25 ml. of benzene was prepared. The mixture was refluxed for 60 minutes and then was cooled and transferred to another flask and kept at room temperature for about 1 hour. Approximately 100 mg. of solid was filtered, and the filtrate was evaporated to give 0.7 grams of the title compound as a slightly yellow foam.

NMR (CDCl$_3$) $\delta$ 4.42 (m,—CH$_2$Br), 5.3 (s, 1H), 5.35 (s,CH$_2$ of pNB), 5.6 (s, 1H), 5.65 (s, 1H), 5.81 (d, 1H, J=4.5 Hz.), 5.9 (d, 1H, J=4.5 Hz.) and 7.4–8.3 Hz. (m, aromatic H).

EXAMPLE 9

Preparation of p-Nitrobenzyl
6-Phthalimido-2$\beta$-chloromethyl-2$\alpha$-methylpenam-3-carboxylate-1$\alpha$-oxide.

To 200 ml. of methylene chloride were added 6.45 grams (12 mmoles) of p-nitrobenzyl 6-phthalimido-2$\beta$-chloromethyl-2$\alpha$-methylpenam-3-carboxylate. An insoluble portion of approximately 100–200 mg. was filtered off, and 2.4 grams (12 mmoles) of m-chloroperbenzoic acid were added. The mixture was stirred for about 30 minutes and then was washed successively with aqueous sodium bicarbonte and aqueous sodium chloride. The mixture was dried over magnesium sulfate and evaporated. The residue was dissolved in a mixture of 10 ml. of methylene chloride and 3 ml. of cyclohexane. The insolubles were filtered off, and the solvent was evaporated to give 5.6 grams of the title compound.

EXAMPLE 10

Preparation of
4-(2'-Benzothiazolyl-dithio)-3-phthalimido-1-[1'-(p-nitrobenzyloxycarbonyl)-2'-chloromethylprop-2'-enyl]-azetidin-2-one.

A mixture of 5.32 grams (10 mmoles) of p-nitrobenzyl 6-phthalimido-2$\beta$-chloromethyl-2$\alpha$-methylpenam-3-carboxylate-1$\alpha$-oxide and 1.7 grams (10 mmoles) of 2-mercaptobenzothiazole in 100 ml. of benzene was prepared. The mixture was refluxed for 50 minutes, and the resulting clear, warm solution was transferred to another flask and was allowed to stand overnight. Crystals (4.5 grams) of the title compound were collected by filtration and shown by TLC to be one spot material.

NMR (CDCl$_3$) $\delta$ 4.23 and 4.5 (dd,-CH$_2$Cl, J=12 Hz), 5.3 (s,1H), 5.33 (s,-CH$_2$ of pNB), 5.5 (s, 1H), 5.6 (s, 1H), 5.75 (d, 1H, J=4.5 Hz.), 5.85 ((d, 1H, J=4.5 Hz.), and 7.4–8.3 Hz. (m, 8 aromatic H).

EXAMPLE 11

Preparation of p-Nitrobenzyl
7-Phthalimido-3-exomethylenecepham-4-carboxylate.

A mixture of 1.3 grams of 4-(2'-benzothiazolyl-dithio)-3-phthalimido-1-[1'-(p-nitrobenzyloxycarbonyl)-2'-chloromethylprop-2'-enyl]azetidin-2-one and 400 mg. of potassium iodide in 70 ml. of acetone was prepared. The mixture was refluxed, and a TLC of the reaction mixture after 19 hours of reflux indicated that approximately one-half of the starting material remained. Refluxing was continued for a total of 44 hours after which time a TLC of the reaction mixture indicated that the starting material was gone. The solution was evaporated, and the residue was dissolved in ethyl acetate. The ethyl acetate solution was washed successively with aqueous sodium thiosulfate, water, aqueous sodium bicarbonate, and aqueous sodium chloride. The ethyl acetate solution then was dried over magnesium sulfate and evaporated to give 0.9 grams of a residue. The residue was dissolved in 5 ml. of toluene after which crystallization began to occur, and 200 mg. of the title compound was collected by filtration and recrystallized from a mixture of 5 ml. of benzene and 2 ml. of chloroform. Crystals of the title compound were collected and again were recrystallized from a mixture of 4 ml. of benzene and 3 ml. of chloroform.

The toluene filtrate was evaporated, and the residue (650 mg.) was chromatographed over a silica gel column (1.5 × 30 cm.) and eluted with a 9:1 mixture of toluene and ethyl acetate to obtain an additional 300 mg. of the title compound.

NMR (CDCl$_3$) $\delta$ 3.3 and 3.62 (dd,-CH$_2$S, J=14 Hz.), 5.37 (s, 5H), 5.43 (d, 1H, J=4.5 Hz.), 5.62 (d, 1H, J=4.5 Hz.), and 7.4–8.3 Hz. (m, 8 aromatic H).

EXAMPLE 12

Preparation of
4-(2'-Benzothiazolyldithio)-3-phthalimido-1-[1'-(p-nitrobenzyloxycarbonyl)-2'-oxo-3'-chloropropyl]azetidin-2-one.

A solution of 650 mg. of 4-(2'-benzothiazolyldithio)-3-phthalimido-1-[1'-(p-nitrobenzyloxycarbonyl)-2'-chloromethylpropy-2'-enyl]azetidine-2-one and 100 ml. of CH$_2$Cl$_2$ was cooled in an acetone-dry ice bath, and ozone was introduced until a blue color appeared (3–5 min.). Sulfur dioxide gas then was passed through the solution for 2 minutes, and the mixture was warmed to room temperature. The mixture then was washed with water and a brine solution. After drying over MgSO$_4$, the solvent was evaporated to yield the title compound.

EXAMPLE 13

Preparation of p-Nitrobenzyl
7-Phthalimido-3-hydroxy-3-cephem-4-carboxylate.

A solution of 350 mg. of p-nitrobenzyl 7-phthalimido-3-exomethylenecepham-4-carboxylate in 100 ml. of chloroform was prepared and then was cooled in a dry ice-acetone bath. Ozone then was passed through the mixture for 2–3 minutes until the color of the mixture turned blue. Sulfur dioxide gas was passed through the solution for about two minutes, and magnesium sulfate then was added to the solution. The solution was brought to room temperature and filtered. The filtrate was evaporated to give 270 mg. of the title compound as a colorless solid containing the corresponding sulfoxide as a minor contaminant.

NMR (CDCl$_3$) δ 2.95 and 4.02 (dd, CH$_2$S, J=15 Hz.), 5.25 (d, 1H, J=4.5 Hz.), 5.4 (s, CH$_2$ of pNB), 5.76 (d, 1H, J=4.5 Hz.), and 7.6–8.3 Hz. (m, 8 aromatic H).

I claim:

1. A process for preparing a cepham compound which comprises reacting a compound of the formula

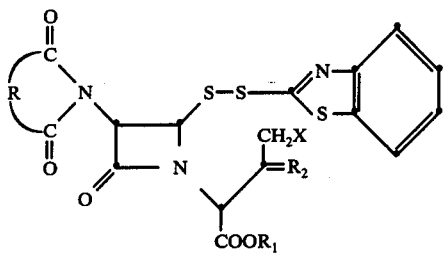

with at least a molar ratio of sodium or potassium iodide at a temperature of from about 40° C. to about 80° C., to produce the 3-exomethylene or 3-keto cepham of the formula

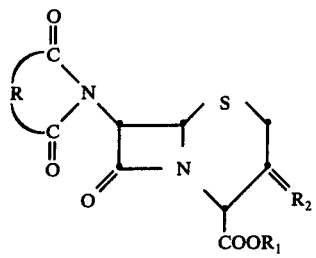

in which, in the above formulae, R$_1$ is a carboxy protecting group; R is the residue of an imide derived from a dicarboxylic acid; R$_2$ is =CH$_2$ or =O; and X is chloro or bromo.

2. Process of claim 1, in which the reaction is carried out in the presence of a ketone solvent.

3. Process of claim 2, in which the reaction is carried out in the presence of acetone.

4. Process of claim 2, in which R$_1$ is the residue of an ester function which is removable by acid treatment or hydrogenation.

5. Process of claim 2, in which R$_1$ is methyl, benzyl, p-nitrobenzyl, p-methoxybenzyl, benzylhydryl, t-butyl, or trimethylsilyl.

6. Process of claim 2, in which R$_1$ is p-nitrobenzyl.

7. Process of claim 2, in which R is phthalimido.

8. Process of claim 7, in which R$_2$ is =CH$_2$.

9. Process of claim 8, in which X is chloro.

10. Process of claim 7, in which R$_2$ is =O.

11. Process of claim 10, in which X is chloro.

* * * * *